United States Patent
Goel et al.

(10) Patent No.: US 11,783,920 B2
(45) Date of Patent: Oct. 10, 2023

(54) SYSTEM AND METHOD FOR EVALUATION OF AT LEAST ONE POTENTIAL TASTANT FROM A PLURALITY OF TASTANTS

(71) Applicant: Tata Consultancy Services Limited, Mumbai (IN)

(72) Inventors: Anukrati Goel, Pune (IN); Kishore Gajula, Pune (IN); Rakesh Gupta, Pune (IN); Beena Rai, Pune (IN)

(73) Assignee: TATA CONSULTANCY SERVICES LIMITED, Mumbai (IN)

( * ) Notice: Subject to any disclaimer, the term of this patent is extended or adjusted under 35 U.S.C. 154(b) by 849 days.

(21) Appl. No.: 16/783,824

(22) Filed: Feb. 6, 2020

(65) Prior Publication Data
US 2020/0251187 A1    Aug. 6, 2020

(30) Foreign Application Priority Data
Feb. 6, 2019    (IN) .............................. 201921004696

(51) Int. Cl.
*G16C 20/10*    (2019.01)
*G16C 20/30*    (2019.01)
(Continued)

(52) U.S. Cl.
CPC ............. *G16C 20/10* (2019.02); *G16C 20/30* (2019.02); *G16C 20/50* (2019.02); *G16C 20/64* (2019.02)

(58) Field of Classification Search
CPC ........ G16C 20/50; G16C 20/10; G16B 40/20; G16B 15/00; G16B 15/30
(Continued)

(56) References Cited

U.S. PATENT DOCUMENTS

| 7,244,584 B2 | 7/2007 | Zuker et al. |
| 2004/0209313 A1 | 10/2004 | Adler |

(Continued)

FOREIGN PATENT DOCUMENTS

| CA | 2402214 | 9/2001 |

OTHER PUBLICATIONS

Raschka, S. (Apr. 2019). "Automated discovery of GPCR bioactive ligands," *Current Opinion in Structural Biology*, vol. 55; pp. 17-24.

*Primary Examiner* — Thinh T Nguyen
(74) *Attorney, Agent, or Firm* — FINNEGAN, HENDERSON, FARABOW, GARRETT & DUNNER, LLP (57) ABSTRACT

A processor implemented method of evaluating at least one potential tastant from a plurality of tastants is provided. The processor implemented method includes at least one of: receiving, information associated with a plurality of molecular activities; generating, a plurality of data-based models based on the known taste index associated with at least one tastant and information from associated molecular structure/descriptors; classifying, a new molecule based on the generated data-based models for the at least one tastant; screening, the one or more classified new molecules in an applicability domain of the generated data-based models based on the physics-based models by at least one molecular modeling technique; and evaluating, the at least one potential tastant from the screened molecules based on at least one of a bioavailability and a toxicity. In an embodiment, the plurality of molecular activities corresponds to a taste index and a binding energy.

18 Claims, 9 Drawing Sheets

(51) Int. Cl.
*G16C 20/64* (2019.01)
*G16C 20/50* (2019.01)

(58) Field of Classification Search
USPC .......................................................... 702/30
See application file for complete search history.

(56) References Cited

U.S. PATENT DOCUMENTS

2005/0244810 A1* 11/2005 Egan et al. ........ G01N 33/5041
435/4
2018/0247076 A1 8/2018 Lerner et al.

* cited by examiner

SYSTEM AND METHOD FOR EVALUATION OF AT LEAST ONE POTENTIAL TASTANT FROM A PLURALITY OF TASTANTS

PRIORITY CLAIM

This U.S. patent application claims priority under 35 U.S.C. § 119 to: India Application No. 201921004696, filed on Feb. 6, 2019. The entire contents of the aforementioned application are incorporated herein by reference.

TECHNICAL FIELD

This disclosure relates generally to evaluation of at least one potential tastant from a plurality of tastants.

BACKGROUND

Currently, food, flavor and fragrance industries spend lots of the efforts on discovery and design of any new molecules/recipes/formulations for their respective purposes. Traditionally, the discovery and design of these formulations are facilitated by detailed experiments with no or very less digital exposure. Once the molecule/recipe/formulation is designed, it further needs to be tested by experts. Further, longer time and high cost associated with experimental route limits the exploration of possible infinite chemical search space. It is imperative to supplement/replace some of the elaborate detailed experimental with in-silico tests due to high costs and time involved in the development and testing of new tastants.

In recent years, some of tastants data-based models are developed, but these models cannot handle inherit complex interaction of tastants with taste receptors. Other limitation of current data-based models is having small dataset for training/developing. The taste is perceived by taste buds present on tongue and it originates from the complex interaction mechanism between taste receptors and the tastants molecule. Further, factorial number of design of experiments have to be carried out for testing/screening of tastants based on their index. Most of the structure activity models to predict taste index are not robust. Most of the developed models for prediction of new tastants are only data based.

SUMMARY

Embodiments of the present disclosure present technological improvements as solutions to one or more of the above-mentioned technical problems recognized by the inventors in conventional systems. For example, in one aspect, a processor implemented method of evaluating at least one potential tastant from a plurality of tastants is provided. The processor implemented method includes at least one of: receiving, via one or more hardware processors, information associated with a plurality of molecular activities; generating, via the one or more hardware processors, a plurality of data-based models based on the known taste index associated with at least one tastant and information from associated molecular structure/descriptors; classifying, via the one or more hardware processors, a new molecule based on the generated data-based models for the at least one tastant; screening, via the one or more hardware processors, the one or more classified new molecules in an applicability domain of the generated data-based models based on the physics-based models by at least one molecular modeling technique; and evaluating, via the one or more hardware processors, the at least one potential tastant from the screened molecules based on at least one of a bioavailability and a toxicity. In an embodiment, the plurality of molecular activities corresponds to a taste index and a binding energy. In an embodiment, the binding energy correspond to one or more interactions between at least one molecule and at least one receptor.

In an embodiment, the plurality of tastants may correspond to a plurality of molecules. In an embodiment, the new molecule may be identified for associated one or more calculated taste class and the taste index. In an embodiment, the one or more calculated taste class associated with the one or more tastants, and the taste index may be identified by testing one or more in silico designed molecular databases. In an embodiment, the one or more taste class may correspond to plurality of taste types. In an embodiment, the plurality of taste types may correspond to at least one of a sweet, a bitter, an umami, and combination thereof. In an embodiment, the generated data-based models may correspond to a model for predicting a relationship based on at least one structure of the plurality of molecules. In an embodiment, in-silico design of one or more molecules may include at least one of (i) template design, and (ii) a molecule fragmentation. In an embodiment, the template design may correspond to creating number of molecules based on at least one particular molecular template by adding one or more functional groups. In an embodiment, the one or more generated models may be tested based on the created number of molecules. In an embodiment, the molecule fragmentation may correspond to slicing one or more functional groups of the one or more molecules to create one or more new molecules for test. In an embodiment, one or more molecules may be screened based on the binding energy with receptor calculated through one or more molecular modelling techniques. In an embodiment, the molecules may be screened by an Absorption, Distribution, Metabolism, Excretion, and Toxicity (ADMET) profile.

In another aspect, there is provided a processor implemented system for evaluation of at least one potential tastant from a plurality of tastants. The system comprises a memory storing instructions; one or more communication interfaces; and one or more hardware processors coupled to the memory via the one or more communication interfaces, wherein the one or more hardware processors are configured by the instructions to: receive, information associated with a plurality of molecular activities; generate, a plurality of data-based models based on the known taste index associated with at least one tastant and information from associated molecular structure/descriptors; classify, a new molecule based on the generated data-based models for the at least one tastant; screen, the one or more classified new molecules in an applicability domain of the generated data-based models based on the physics-based models by at least one molecular modeling technique; and evaluate, the at least one potential tastant from the screened molecules based on at least one of a bioavailability and a toxicity. In an embodiment, the plurality of molecular activities corresponds to a taste index and a binding energy. In an embodiment, the binding energy correspond to one or more interactions between at least one molecule and at least one receptor.

In an embodiment, the plurality of tastants may corresponds to a plurality of molecules. In an embodiment, the new molecule may be identified for associated one or more calculated taste class and the taste index. In an embodiment, the one or more calculated taste class associated with the one or more tastants, and the taste index may be identified by testing one or more in silico designed molecular databases. In an embodiment, the one or more taste class may correspond to plurality of taste types. In an embodiment, the plurality of taste types may correspond to at least one of a sweet, a bitter, an umami, and combination thereof. In an embodiment, the generated data-based models may correspond to a model for predicting a relationship based on at least one structure of the plurality of molecules. In an embodiment, in-silico design of one or more molecules may include at least one of (i) template design, and (ii) a molecule fragmentation. In an embodiment, the template design may correspond to creating number of molecules based on at least one particular molecular template by adding one or more functional groups. In an embodiment, the one or more generated models may be tested based on the created number of molecules. In an embodiment, the molecule fragmentation may correspond to slicing one or more functional groups of the one or more molecules to create one or more new molecules for test. In an embodiment, one or more molecules may be screened based on the binding energy with receptor calculated through one or more molecular modelling techniques. In an embodiment, the molecules may be screened by an Absorption, Distribution, Metabolism, Excretion, and Toxicity (ADMET) profile.

In yet another aspect, there are provided one or more non-transitory machine-readable information storage mediums comprising one or more instructions which when executed by one or more hardware processors causes at least one of: receiving, information associated with a plurality of molecular activities; generating, a plurality of data-based models based on the known taste index associated with at least one tastant and information from associated molecular structure/descriptors; classifying, a new molecule based on the generated data-based models for the at least one tastant; screening, the one or more classified new molecules in an applicability domain of the generated data-based models based on the physics-based models by at least one molecular modeling technique; and evaluating, the at least one potential tastant from the screened molecules based on at least one of a bioavailability and a toxicity. In an embodiment, the plurality of molecular activities corresponds to a taste index and a binding energy. In an embodiment, the binding energy correspond to one or more interactions between at least one molecule and at least one receptor.

In an embodiment, the plurality of tastants may corresponds to a plurality of molecules. In an embodiment, the new molecule may be identified for associated one or more calculated taste class and the taste index. In an embodiment, the one or more calculated taste class associated with the one or more tastants, and the taste index may be identified by testing one or more in silico designed molecular databases. In an embodiment, the one or more taste class may correspond to plurality of taste types. In an embodiment, the plurality of taste types may correspond to at least one of a sweet, a bitter, an umami, and combination thereof. In an embodiment, the generated data-based models may correspond to a model for predicting a relationship based on at least one structure of the plurality of molecules. In an embodiment, in-silico design of one or more molecules may include at least one of (i) template design, and (ii) a molecule fragmentation. In an embodiment, the template design may correspond to creating number of molecules based on at least one particular molecular template by adding one or more functional groups. In an embodiment, the one or more generated models may be tested based on the created number of molecules. In an embodiment, the molecule fragmentation may correspond to slicing one or more functional groups of the one or more molecules to create one or more new molecules for test. In an embodiment, one or more molecules may be screened based on the binding energy with receptor calculated through one or more molecular modelling techniques. In an embodiment, the molecules may be screened by an Absorption, Distribution, Metabolism, Excretion, and Toxicity (ADMET) profile.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this disclosure, illustrate exemplary embodiments and, together with the description, serve to explain the disclosed principles.

DETAILED DESCRIPTION

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the scope of the disclosed embodiments. It is intended that the following detailed description be considered as exemplary only, with the true scope being indicated by the following claims.

Embodiments herein provides a system and method for evaluation of plurality of tastants based on taste index, binding energy and interaction parameters. The embodiments of the present disclosure provide a framework to virtually screen tastants from plurality of databases. A data-based models are developed to calculate taste index of a tastant. The plurality of databases of natural compounds are checked for applicability domain and are screened based on similarity search and the taste index. The tastants in an applicability domain of the developed data-based models (e.g., structure activity relationship models) are screened through physics-based models developed at molecular scale. These are further screened based on an Absorption, Distribution, Metabolism, Excretion, and Toxicity (ADMET) profile. The screened tastants from both the data-based model and a physics-based model further can be designed and tested in laboratory.

Referring now to the drawings, and more particularly to FIG. 1 through FIG. 7, where similar reference characters denote corresponding features consistently throughout the figures, there are shown preferred embodiments and these embodiments are described in the context of the following exemplary system and/or method.

Figure 1:
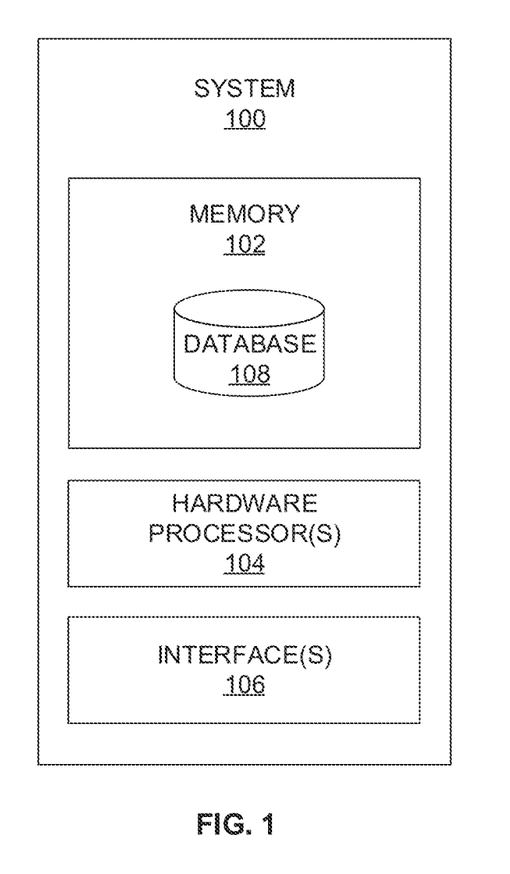
FIG. 1 illustrates a system for evaluation of at least one potential tastant from a plurality of tastants based on plurality of parameters according to embodiments of the present disclosure.

FIG. 1 illustrates a system for evaluation of at least one potential tastant from a plurality of tastants based on plurality of parameters according to embodiments of the present disclosure. In an embodiment, the system 100 includes one or more processors 104, communication interface device(s) or input/output (I/O) interface(s) 106, and one or more data storage devices or memory 102 operatively coupled to the one or more processors 104. The memory 102 comprises a database 108. The one or more processors 104 that are hardware processors can be implemented as one or more microprocessors, microcomputers, microcontrollers, digital signal processors, central processing units, state machines, logic circuitries, and/or any devices that manipulate signals based on operational instructions. Among other capabilities, the processor(s) is configured to fetch and execute computer-readable instructions stored in the memory. In an embodiment, the system 100 can be implemented in a variety of computing systems, such as laptop computers, notebooks, hand-held devices, workstations, mainframe computers, servers, a network cloud and the like.

The I/O interface device(s) 106 can include a variety of software and hardware interfaces, for example, a web interface, a graphical user interface, and the like and can facilitate multiple communications within a wide variety of networks N/W and protocol types, including wired networks, for example, LAN, cable, etc., and wireless networks, such as WLAN, cellular, or satellite. In an embodiment, the I/O interface device(s) can include one or more ports for connecting a number of devices to one another or to another server.

The memory 102 may include any computer-readable medium known in the art including, for example, volatile memory, such as static random access memory (SRAM) and dynamic random access memory (DRAM), and/or non-volatile memory, such as read only memory (ROM), erasable programmable ROM, flash memories, hard disks, optical disks, and magnetic tapes. In an embodiment, the memory 102 includes a plurality of modules and a repository for storing data processed, received, and generated by the plurality of modules. The plurality of modules may include routines, programs, objects, components, data structures, and so on, which perform particular tasks or implement particular abstract data types.

Further, the database 108 stores information pertaining to inputs fed to the system 100 and/or outputs generated by the system 100 (e.g., data/output generated at each stage of the data processing), specific to the methodology described herein. More specifically, the database 108 stores information being processed at each step of the proposed methodology.

The repository, amongst other things, includes a system database and other data. The other data may include data generated as a result of the execution of one or more modules in the plurality of modules.

The database 108 may store information but are not limited to, information associated with at least one of: (i) data based models, (ii) physics based models, and (iii) plurality of molecules obtained from one or more module e.g., organic molecules, in-organic molecules, and biomolecules. Further, the database 108 stores information pertaining to inputs fed to the system 100 and/or outputs generated by the system (e.g., at each stage), specific to the methodology described herein. More specifically, the database 108 stores information being processed at each step of the proposed methodology.

Figure 2:
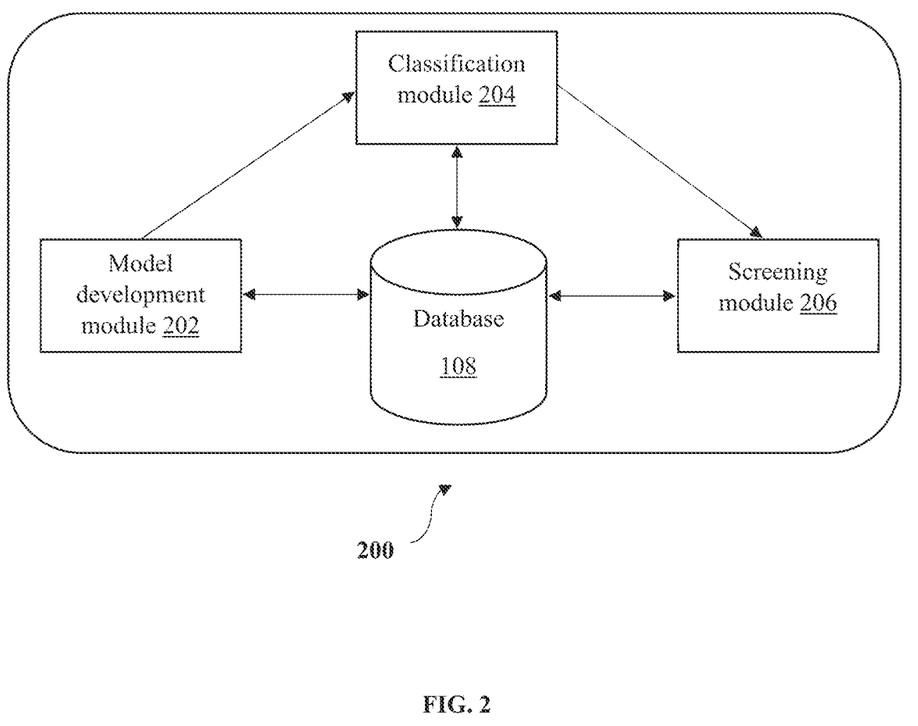
FIG. 2 is an exploded view of the exemplary system illustrates evaluation of the at least one potential tastant from the plurality of tastants based on plurality of parameters according to embodiments of the present disclosure.

FIG. 2 is an exploded view of the exemplary system illustrates evaluation of the at least one potential tastant from the plurality of tastants based on plurality of parameters according to embodiments of the present disclosure. The exploded view of the system 200 includes a model development module 202, a classification module 204, and a screening module 206. In an embodiment, a framework which corresponds to the system 200. In an embodiment, the framework is configured to discover, design, classification, and testing of plurality of tastants utilizing both data-based models and physics driven models. The framework includes data-based models which calculate taste index of tastants and physio-chemical properties responsible for activity. In an embodiment, the plurality of tastants corresponds to plurality of molecules. In an exemplary embodiment, the data-based models correspond to but not limited to at least one of (i) structure property relationship models, (ii) machine learning models, (iii) a sweet, a bitter, an umami models, and combination thereof. In an embodiment, the machine learning models are linear regression models or nonlinear regression models. For example, the nonlinear regression models can be artificial neural networks (ANN), Support vector machine (SVM), and Random forest (RF).

In an embodiment, the data-based models are developed in the model development module 202 to predict activity or properties of tastants. In another embodiment, the data-based models are developed using tastants with known taste index and information from associated molecular structure. In an embodiment, the plurality of parameters corresponds to but not limited to at least one of (a) a taste index, and (b) a binding energy, and combination thereof.

The classification module 204 is configured to classify/test new molecules based on the developed data-based models for different tastants. In an embodiment, the data-based models are configured to identify a qualitative nature or class of tastants using the classification module 204. The classification module 204 is configured to identify the class of unknown compound and corresponding taste intensity are be identified. For example, the new molecules are identified for associated taste class and taste index is calculated. In an embodiment, available databases or in-silico designed molecular database are tested to identify their class and taste index before screening them by the screening module 206. In an embodiment, the plurality of databases of natural compounds is screened based on applicability and class. In an embodiment, the class corresponds to plurality of taste types e.g., a sweet, a sour, a bitter, an umami and combination thereof.

In an embodiment, in-silico design of molecules which includes template design and molecule fragmentation. In an embodiment, the template design corresponds to creating number of molecules based on one particular molecular template by adding other functional groups. Further, the created molecules can be used for testing the models developed. In an embodiment, the molecule fragmentation corresponds to chopping off some functional groups of molecules thereby creating new molecules, which can be tested.

The molecules screened from previous step are screened based on the binding energy with receptor calculated through one or more molecular modelling techniques e.g., molecular docking. The detailed analysis of binding sites are performed for screened candidates, which can be potential tastants. In an embodiment, the oral bioavailability of compounds is accessed based on at least one of methodology and techniques. For example, the molecules are screened by Absorption, Distribution, Metabolism, Excretion, and Toxicity (ADMET) profile.

The molecules tested in the classification module 204 are screened using the screening module 206 to identify potential tastants from the plurality of databases. The screening module 206 includes many filtering tools using insights both from the data and the physics-based models along with bioavailability and toxicity of compound. The screening module 206 includes three screening stages wherein the molecules tested in the classification module 204 are screened based on insights from both, the data-based models and the physics-based models. In an embodiment, a similarity search, the first stage checks for the applicability domain of the molecules. In an embodiment, the molecules in an applicability domain of the developed model are further screened based on physics-based models developed using molecular modelling techniques. For example, the molecular modelling techniques are at least one of a Monte Carlo simulation, molecular dynamics. The molecular modeling screens the molecules using insights from type of interactions between tastants with taste receptors. The molecules are finally screened based on their bioavailability and toxicity, which then can further be designed/synthesized or tested in laboratory.

Figure 3A:
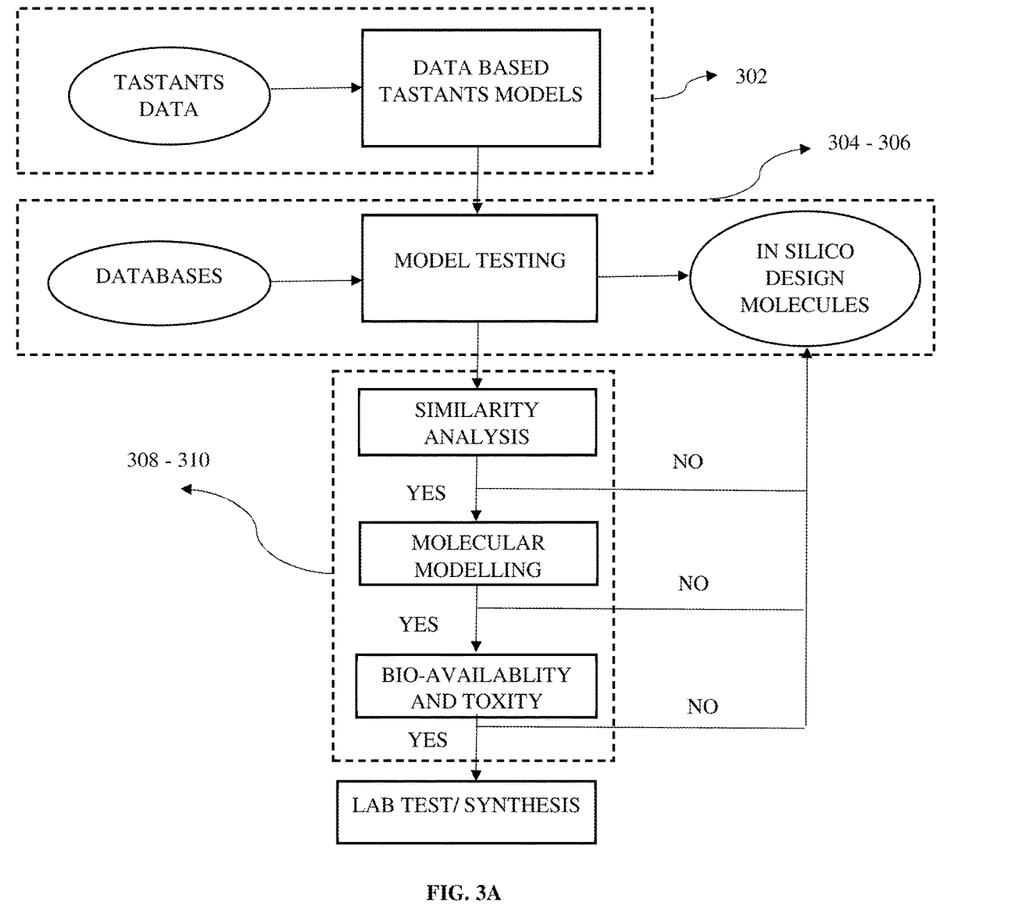
FIG. 3A and FIG. 3B are flow diagrams illustrating a method of evaluating plurality of tastants based on plurality of parameters according to embodiments of the present disclosure.
Figure 3B:
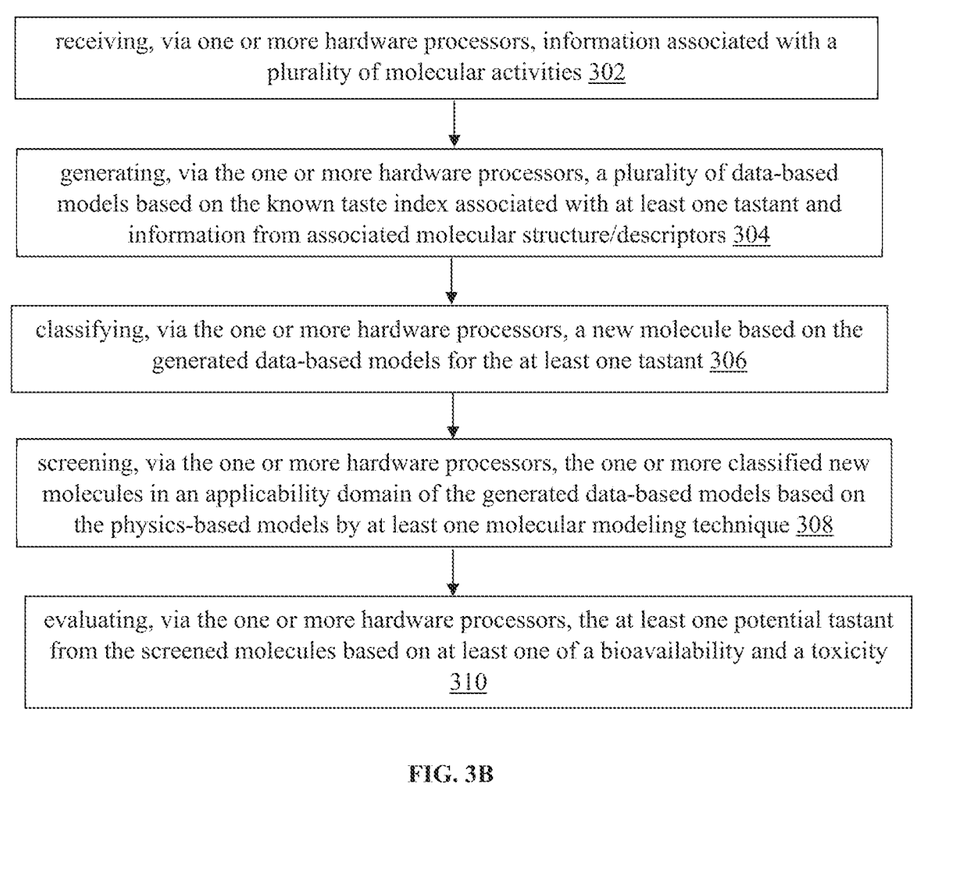

FIG. 3A and FIG. 3B are flow diagrams illustrating a method of evaluating plurality of tastants based on plurality of parameters according to embodiments of the present disclosure. In an embodiment, evaluating plurality of tastants based on molecular activities i.e., taste index and interactions between molecules and receptors i.e., binding energy. In an embodiment, the plurality of tastants corresponds to a plurality of molecules. In step 302, information associated with a plurality of molecular activities are received. In an embodiment, the plurality of molecular activities corresponds to a taste index and a binding energy. In an embodiment, the binding energy correspond to one or more interactions between at least one molecule and at least one receptor. In an embodiment, the data-based models are developed in the model development module 202 based on tastants with known taste index and information from associated molecular structure/descriptors.

In step 304, a plurality of data-based models is generated based on the known taste index associated with at least one tastant and information from associated molecular structure/descriptors. In an embodiment, the classification or testing of a new molecule based on the developed data-based models (e.g., structure property relationship models) for different tastants. The new molecule is identified for associated taste class and taste index. In an embodiment, the available databases or in silico designed molecular database are tested to identify their class and taste index before screening them by the screening module 206. In step 306, a new molecule is classified based on the generated data-based models for the at least one tastant. In an embodiment, the molecules tested in the classification module 204 are screened by the screening module 206 based on insights from both, the data-based models and the physics-based models. In step 308, the one or more classified new molecules in an applicability domain of the generated database-based models is screened based on the physics-based models by at least one molecular modeling technique. In an embodiment, the molecules in an applicability domain of the developed model are further screened based on the physics-based models by at least one of the molecular modeling techniques. The molecular modeling screens the molecules using insights from interaction between tastants and receptor. In step 310, evaluating, via the one or more hardware processors, the at least one potential tastant from the screened molecules based on at least one of a bioavailability and a toxicity. In an embodiment, the molecules are finally screened based on their bioavailability and toxicity, which then are designed or tested in a laboratory.

In an embodiment, the plurality of tastants may correspond to a plurality of molecules. In an embodiment, the new molecule may be identified for associated one or more calculated taste class and the taste index. In an embodiment, the one or more calculated taste class associated with the one or more tastants, and the taste index may be identified by testing one or more in silico designed molecular databases. In an embodiment, the one or more taste class may correspond to plurality of taste types. In an embodiment, the plurality of taste types may correspond to at least one of a sweet, a bitter, an umami, and combination thereof. In an embodiment, the generated data-based models may correspond to a model for predicting a relationship based on at least one structure of the plurality of molecules. In an embodiment, in-silico design of one or more molecules may include at least one of (i) template design, and (ii) a molecule fragmentation.

In an embodiment, the template design may correspond to creating number of molecules based on at least one particular molecular template by adding one or more functional groups. In an embodiment, the one or more generated models may be tested based on the created number of molecules. In an embodiment, the molecule fragmentation may correspond to slicing one or more functional groups of the one or more molecules to create one or more new molecules for test. In an embodiment, one or more molecules may be screened based on the binding energy with receptor calculated through one or more molecular modelling techniques. In an embodiment, the molecules may be screened by an Absorption, Distribution, Metabolism, Excretion, and Toxicity (ADMET) profile.

Experimental Results:

The system 100 provide evaluating at least one potential tastant from a plurality of tastants. In an exemplary embodiment, a large database of natural compounds is screened to discover new sweeteners. For example, one or more chemical spaces and 487 sweeteners were compared to remove structurally dissimilar natural molecules, i.e. having a Tanimoto coefficient of less than 0.65. The pairwise chemical similarity between the database of natural compounds and the 487 sweeteners is computed based on standard fingerprints of 1024 bits using R package rcdk34. The database of natural compounds includes a very high diverse class of natural compounds in comparison to the 487 sweeteners used to develop a (QSAR) model, only 10,184 out of 213,210 natural compounds found to be structurally similar to the 487 sweeteners. This proportionate to a very small fraction ~5% of molecules virtually screened to identify new potential sweeteners. The chemically similar 10184 molecules are further screened to remove molecules sharing undesirable bitter taste using the developed classification model discriminating sweet and bitter taste. The compound considered to be sweet if the predicted classification confidence for sweet class was greater than 0.7. Around 1924 out of 10184 similar natural molecules, i.e. ~19% were classified in cluster of sweet taste.

The identified sweeteners are subjected to developed sweet intensity prediction model to predict associated sweetness index. Out of 1924 sweet molecules screened, 1354 molecules exhibited significantly high sweetness index, log (RS)>3.0. Additionally, the identified sweeteners containing undesirable scaffolds involved in toxicity were also excluded. In an embodiment, pkCSM36 is used to assess various toxicological parameters resulting in 60 molecules having accepted oral bioavailability with no toxicity.

In an embodiment, chemical formulae of the 60 molecules are provided below:

$(C_{42}H_{66}O_{15}, C_{41}H_{64}O_{14}, C_{32}H_{52}O_{13}, C_{42}H_{66}O_{15}, C_{42}H_{66}O_{13}, C_{42}H_{62}O_{16}, C_{42}H_{66}O_{15}, C_{42}H_{66}O_{14}, C_{32}H_{50}O_{13}, C_{19}H_{36}O_8, C_{31}H_{50}O_{13}, C_{32}H_{50}O_{13}, C_{41}H_{62}O_{14}, C_{41}H_{62}O_{16}, C_{42}H_{66}O_{14}, C_{41}H_{62}O_{14}, C_{42}H_{66}O_{15}, C_{32}H_{50}O_{13}, C_{42}H_{68}O_{14}, C_{16}H_{30}O_6, C_{42}H_{62}O_{16}, C_{32}H_{50}O_{13}, C_{40}H_{64}O_{13}, C_{42}H_{62}O_{16}, C_{41}H_{64}O_{13}, C_{41}H_{64}O_{14}, C_{42}H_{62}O_{16}, C_{39}H_{62}O_{13}, C_{41}H_{64}O15, C_{41}H_{64}O_{14}, C_{42}H_{62}O_{16}, C_{19}H_{36}O_7, C_{38}H_{64}O_{10}, C_{33}H_{52}O_{14}, C_{39}H_{62}O_{13}, C_{42}H_{66}O_{15}, C_{42}H_{68}O_{14}, C_{41}H_{64}O_{14}, C_{41}H_{64}O_{14}, C_{41}H_{62}O_{16}, C_{41}H_{58}O_{18}, C_{43}H_{66}O_{14}, C_{31}H_{50}O_{12}, C_{41}H_{64}O_{14}, C_{42}H_{62}O_{16}, C_{41}H_{64}O_{14}, C_{39}H_{62}O_{13}, C_{42}H_{66}O_{14}, C_{27}H_{42}O_9, C_{19}H_{36}O_8, C_{19}H_{36}O_7, C_{42}H_{62}O_{16}, C_{40}H_{64}O_{13}, C_{32}H_{50}O_{13}, C_{41}H_{68}O_{13}, C_{41}H_{64}O_{14}, C_{41}H_{62}O_{14}, C_{41}H_{64}O_{15}, C_{39}H_{62}O_{13}, C_{41}H_{58}O_{18})$.

The screened sweet molecules with accepted toxicity profile were forwarded for docking analysis. The binding conformation and binding energy for the screened 60 molecules was calculated by molecular docking using the disclosed protocol. Since the correlation between the binding energy and the sweetness index is observed to be moderate, they were not ranked based on their affinity for the receptor. However, docking studies on new identified natural sweeteners revealed that these molecules also have quite high binding in line with terpenes and a polyphenols. For example, the identified natural high potent sweeteners belong to family of the terpene and less than 7% molecules were polyphenols or phenylpropanoids. The identified new sweeteners share the same binding cavity and possess high molecular weight, number of hydrogen bond donors and acceptors and number of rings correspondent to the already known natural sweeteners.

The identified new sweeteners possess high sweetness index but still were less sweet than the synthesized molecules derived from guanidine or amino L-aspartyl dipeptides. The observation that physio chemical properties for these natural sweeteners go beyond the upper bound described for most intense sweeteners. The scaffold of existing sweeteners can be rationally modified (functionalized by a limited number of rings, hydrogen bonding sites with a moderate molecular weight) to create a virtual library of molecules for high throughput screening. In addition to this, molecular dynamics or ab-initio simulations need to be performed to understand molecular basis of differences in sweetness activity. A resolved crystallographic structure of sweet taste receptor said significantly to elucidate perception of sweet taste and designing a potential sweetener.

The molecules lying in the applicability domain of developed QSAR model were screened based on the predicted sweetness index. For example, additional filters were applied to remove compounds sharing undesirable bitter taste and exhibiting toxicological profile. For structure-based design, a computational ligand-target docking approach used to analyze ligand-receptor complex and binding affinity of sweeteners for the receptor. The new identified sweeteners can be further tested using computational or experimental techniques in quest for an ideal low calorific sweetener. The embodiments of the present disclosure significantly reduce the time and testing expenses incurred on experiments.

Figure 4:
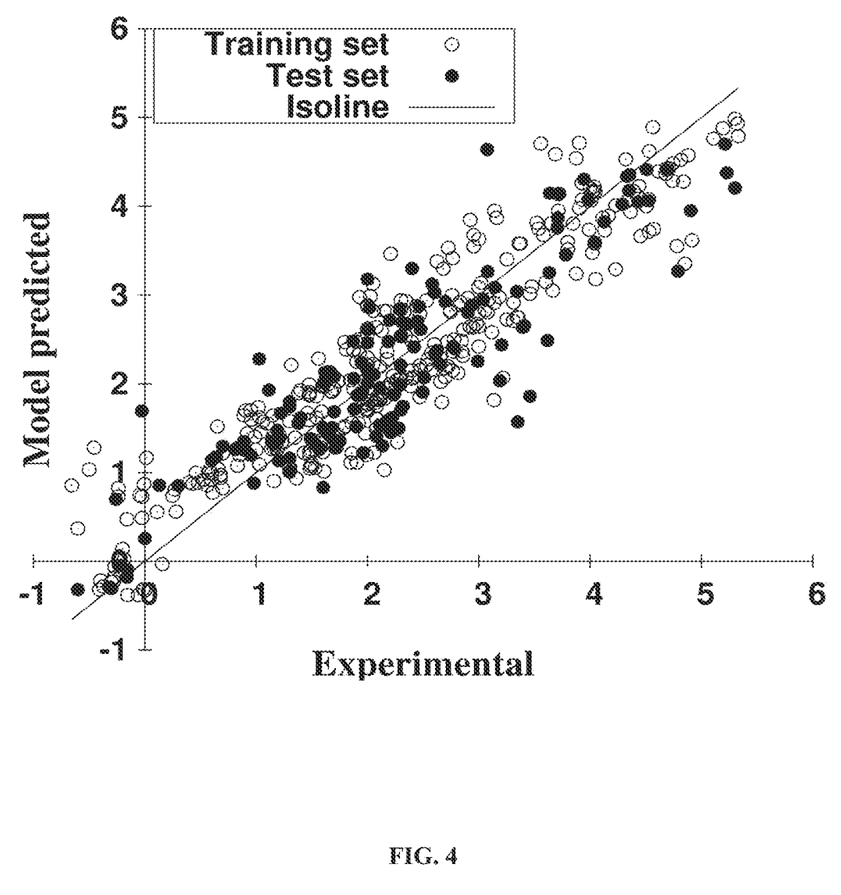
FIG. 4 illustrates a graphical representation of model predicted log (RS) value for training and test set according to embodiments of the present disclosure.

FIG. 4 illustrates a graphical representation of model predicted log (RS) value for training and test set according to embodiments of the present disclosure. The graphical representation of a parity plot of observed relative sweetness of the tastants against experimental sweetness of tastants. In an embodiment, RS refers to the relative sweetness of the tastants. In an embodiment, the observed relative sweetness values are predicted from the data-based models. In an embodiment, the experimental relative sweetness values are obtained from one or more conventional techniques.

Figure 5:
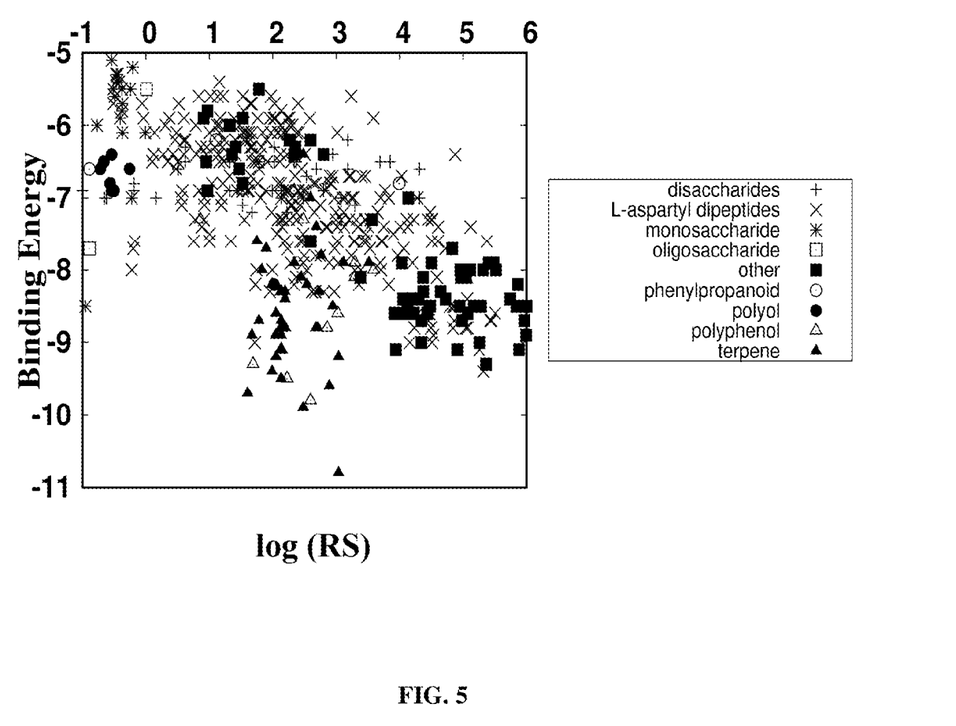
FIG. 5 illustrates a graphical representation of plot of binding energy (kcal/mol) versus sweetness index log (RS) for different class of sweeteners according to embodiments of the present disclosure.
Figure 6A:
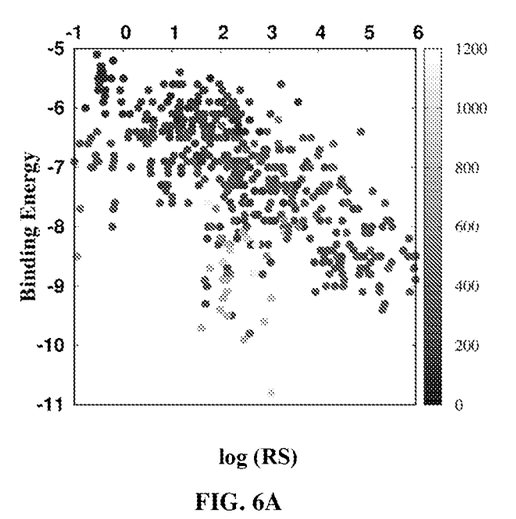
FIGS. 6A-6D illustrates a graphical representation of plot of binding energy (kcal/mol) versus sweetness index log (RS) on the basis of physiochemical properties, (a) molecular weight, (b) number of rings, (c) number of hydrogen bond donors and (d) polar surface area, according to embodiments of the present disclosure.
Figure 6B:
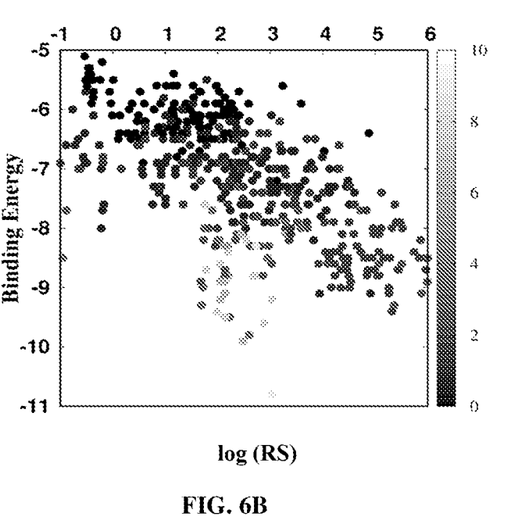
Figure 6C:
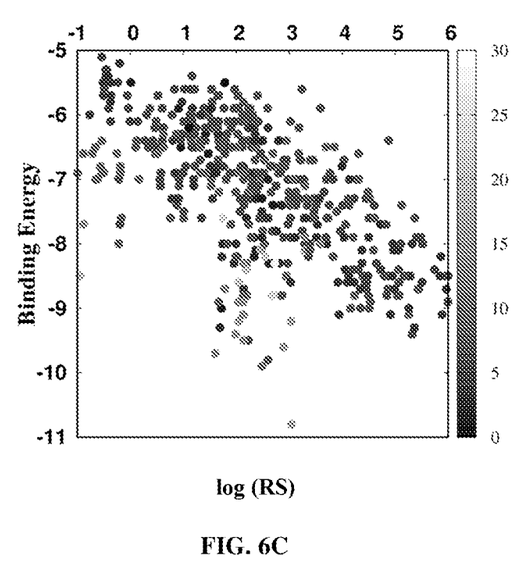
Figure 6D:
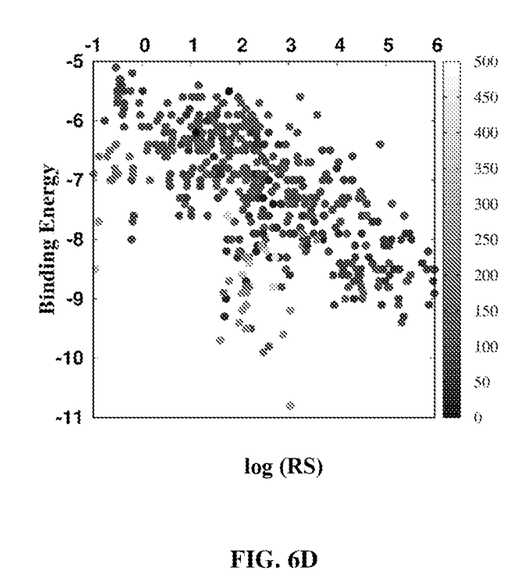

FIG. 5 illustrates a graphical representation of plot of binding energy (kcal/mol) versus sweetness index log (RS) for different class of sweeteners according to embodiments of the present disclosure. The graphical representation of a relative sweetness of tastants against binding energy of the tastant molecule with taste receptor. In an embodiment, the relative sweetness (RS) values being the experimental value obtained from one or more conventional techniques. In an embodiment, the binding energy values are calculated using molecular docking simulations.

FIGS. 6A-6D illustrates a graphical representation of plot of binding energy (kcal/mol) versus sweetness index log (RS) on the basis of physiochemical properties, (a) molecular weight, (b) number of rings, (c) number of hydrogen bond donors and (d) polar surface area according to embodiments of the present disclosure.

Figure 7:
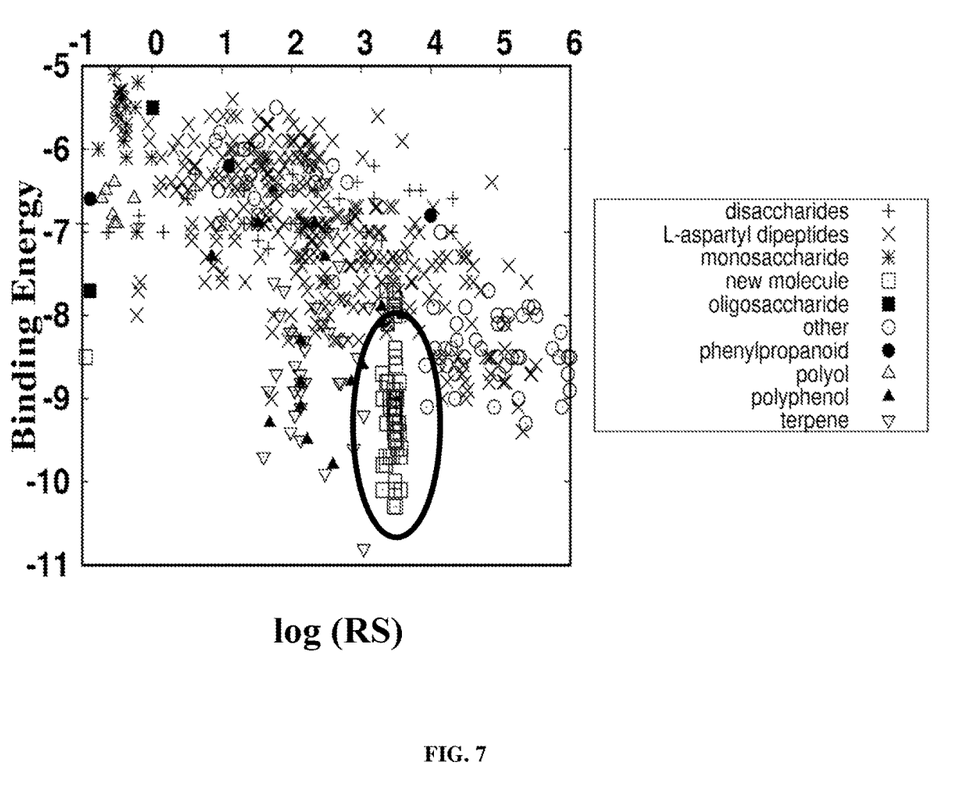
FIG. 7 illustrates a graphical representation of plot of binding energy (kcal/mol) versus sweetness index log (RS) for different class of sweeteners according to embodiments of the present disclosure.

FIG. 7 illustrates a graphical representation of plot of binding energy (kcal/mol) versus sweetness index log(RS) for different class of sweeteners according to embodiments of the present disclosure. In an embodiment, the new molecules are encircled.

The embodiments of present disclosure herein propose a framework, which utilizes both data based and physics-based models for in-silico tastants discovery, design and testing. The embodiments of present disclosure utilize both data based and physics-based models for taste calculation. This framework enables a support in speeding process of tastant design and development process. The framework reduces the factorial design of experiments needed to design, develop and test the tastants. The present invention provides molecular features responsible for activity and molecular level information of binding with taste receptor.

The embodiments of present disclosure calculate new tastants on the based on insights from both molecular structure and interaction with taste receptor. The embodiments of present disclosure provide a module to calculate the interaction and binding sites of tastants with taste receptor. The embodiments of present disclosure herein provide a module to calculate bioavailability and toxicity of tastants. The embodiments of present disclosure provide a framework which includes a robust data-based model to calculate plurality of tastants from a large database.

The embodiments of present disclosure provide a framework which is a systematic approach instead of hit and trial approach. The embodiments of present disclosure also consider one or more physio-kinetic properties into account. In addition to this, bioavailability of tastants in the body is analyzed. The ADMET (Absorption, Distribution, Metabolism, Excretion, and Toxicity) studies for predicted tastants are performed for checking their bioavailability and toxicity. The model and methodology are used in the design and development of potential tastants for virtual testing/screening of the candidates. This procedure saves computational time from the current experimental methods. The embodiments of present disclosure utilize both data and physics-based models and oral bioavailability to virtually screen a large database to predict potential tastants. The developed protocol and methods could significantly reduce the time and testing expenses incurred on experiments.

The written description describes the subject matter herein to enable any person skilled in the art to make and use the embodiments. The scope of the subject matter embodiments is defined by the claims and may include other modifications that occur to those skilled in the art. Such other modifications are intended to be within the scope of the claims if they have similar elements that do not differ from the literal language of the claims or if they include equivalent elements with insubstantial differences from the literal language of the claims.

It is to be understood that the scope of the protection is extended to such a program and in addition to a computer-readable means having a message therein; such computer-readable storage means contain program-code means for implementation of one or more steps of the method, when the program runs on a server or mobile device or any suitable programmable device. The hardware device can be any kind of device which can be programmed including e.g. any kind of computer like a server or a personal computer, or the like, or any combination thereof. The device may also include means which could be e.g. hardware means like e.g. an application-specific integrated circuit (ASIC), a field-programmable gate array (FPGA), or a combination of hardware and software means, e.g. an ASIC and an FPGA, or at least one microprocessor and at least one memory with software processing components located therein. Thus, the means can include both hardware means and software means. The method embodiments described herein could be implemented in hardware and software. The device may also include software means. Alternatively, the embodiments may be implemented on different hardware devices, e.g. using a plurality of CPUs.

The embodiments herein can comprise hardware and software elements. The embodiments that are implemented in software include but are not limited to, firmware, resident software, microcode, etc. The functions performed by various components described herein may be implemented in other components or combinations of other components. For the purposes of this description, a computer-usable or computer readable medium can be any apparatus that can comprise, store, communicate, propagate, or transport the program for use by or in connection with the instruction execution system, apparatus, or device.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include random access memory (RAM), read-only memory (ROM), volatile memory, nonvolatile memory, hard drives, CD ROMs, DVDs, flash drives, disks, and any other known physical storage media.

It is intended that the disclosure and examples be considered as exemplary only, with a true scope of disclosed embodiments being indicated by the following claims.

What is claimed is:

1. A processor implemented method of evaluating at least one potential tastant from a plurality of tastants, comprising:

receiving, via one or more hardware processors, information associated with a plurality of molecular activities, wherein the plurality of molecular activities corresponds to a taste index and a binding energy, wherein the binding energy correspond to one or more interactions between at least one molecule and at least one receptor;

generating, via the one or more hardware processors, a plurality of data-based models based on the known taste index associated with at least one tastant and information from associated molecular structure/descriptors, wherein the data-based models correspond to at least one of (i) structure property relationship models, (ii) machine learning models corresponding to a linear regression models or non-linear regression models;

classifying, via the one or more hardware processors, a new molecule based on the generated data-based models for the at least one tastant;

screening, via the one or more hardware processors, the one or more classified new molecules in an applicability domain of the generated data-based models based on physics-based models, developed at molecular scale, by at least one molecular modeling technique, wherein the molecular modelling techniques include at least one of a Monte Carlo simulation and molecular dynamics, wherein the molecular modeling technique screens the one or more classified new molecules using insights from the interaction of the at least one tastant with the at least one receptor;

evaluating, via the one or more hardware processors, the at least one potential tastant from the screened molecules based on at least one of a bioavailability and a toxicity; and providing a framework to virtually screen the plurality of tastants from a plurality of databases and utilizes both the data-based models and the physics-based models for in-silico tastants discovery, design, classification, and testing the plurality of tastants, wherein the framework, with a systematic approach, supports in speeding process of tastant design, development process.

2. The processor implemented method of claim 1, wherein the plurality of tastants corresponds to a plurality of molecules.

3. The processor implemented method of claim 1, wherein the new molecule is identified for associated one or more calculated taste class and the taste index, wherein, the one or more calculated taste class associated with the one or more tastants, and the taste index are identified by testing one or more in silico designed molecular databases.

4. The processor implemented method of claim 3, wherein the one or more taste class corresponds to plurality of taste types, wherein the plurality of taste types corresponds to at least one of a sweet, a bitter, an umami, and combination thereof.

5. The processor implemented method of claim 1, wherein the generated data-based models correspond to a model for predicting a relationship based on at least one structure of the plurality of molecules.

6. The processor implemented method of claim 1, wherein in-silico design of one or more molecules comprises at least one of (i) template design, and (ii) a molecule fragmentation.

7. The processor implemented method of claim 1, wherein the template design corresponds to creating number of molecules based on at least one particular molecular template by adding one or more functional groups, wherein the one or more generated models are tested based on the created number of molecules.

8. The processor implemented method of claim 6, wherein the molecule fragmentation corresponds to slicing one or more functional groups of the one or more molecules to create one or more new molecules for test.

9. The processor implemented method of claim 1, wherein the bioavailability and toxicity of the screened molecules are checked using an Absorption, Distribution, Metabolism, Excretion, and Toxicity (ADMET) profile.

10. A system (100) for executing a method of claim 1, wherein the system comprises:
a memory (102) storing instructions; and
one or more hardware processors (104) coupled to the memory (102), wherein the one or more hardware processors (104) are configured by the instructions to:
receive, information associated with a plurality of molecular activities, wherein the plurality of molecular activities corresponds to a taste index and a binding energy, wherein the binding energy correspond to one or more interactions between at least one molecule and at least one receptor;
generate, a plurality of data-based models based on the known taste index associated with at least one tastant and information from associated molecular structure/descriptors;
classify, a new molecule based on the generated data-based models for the at least one tastant;
screen, the one or more classified new molecules in an applicability domain of the generated data-based models based on the physics-based models by at least one molecular modeling technique; and
evaluate, the at least one potential tastant from the screened molecules based on at least one of a bioavailability and a toxicity.

11. The system of claim 10, wherein the plurality of tastants corresponds to a plurality of molecules.

12. The system of claim 10, wherein the new molecule is identified for associated one or more calculated taste class and the taste index, wherein, the one or more calculated taste class associated with the one or more tastants, and the taste index are identified by testing one or more in silico designed molecular databases.

13. The system of claim 12, wherein the one or more taste class corresponds to plurality of taste types, wherein the plurality of taste types corresponds to at least one of a sweet, a bitter, an umami, and combination thereof.

14. The system of claim 10, wherein the generated data-based models correspond to a model for predicting a relationship based on at least one structure of the plurality of molecules.

15. The system of claim 10, wherein in-silico design of one or more molecules comprises at least one of (i) template design, and (ii) a molecule fragmentation.

16. The system of claim 10, wherein the template design corresponds to creating number of molecules based on at least one particular molecular template by adding one or more functional groups, wherein the one or more generated models are tested based on the created number of molecules.

17. The system of claim 10, wherein the molecule fragmentation corresponds to slicing one or more functional groups of the one or more molecules to create one or more new molecules.

18. The system of claim 10, wherein one or more molecules are screened based on the binding energy with receptor calculated through one or more molecular modelling techniques, wherein the molecules are screened by an Absorption, Distribution, Metabolism, Excretion, and Toxicity (ADMET) profile.

* * * * *